United States Patent [19]
Therien et al.

[11] Patent Number: 6,100,392
[45] Date of Patent: Aug. 8, 2000

[54] ELECTRON-DEFICIENT PORPHYRINS AND PROCESSES AND INTERMEDIATES FOR PREPARING SAME

[75] Inventors: Michael J. Therien, Philadelphia, Pa.; Stephen DiMagno, Lincoln, Nebr.

[73] Assignee: The Trustees of the University of Pennsylavania, Philadelphia, Pa.

[21] Appl. No.: 09/129,620

[22] Filed: Aug. 5, 1998

Related U.S. Application Data

[60] Division of application No. 08/763,766, Dec. 11, 1996, and a continuation-in-part of application No. 08/064,468, May 20, 1993, Pat. No. 5,493,017, which is a continuation-in-part of application No. 07/929,943, Aug. 14, 1992, Pat. No. 5,371,199.

[51] Int. Cl.$^7$ .................................................. C07D 487/22
[52] U.S. Cl. ........................................... 540/145; 568/910
[58] Field of Search .............................. 540/145; 568/910

[56] References Cited

U.S. PATENT DOCUMENTS

| | | | |
|---|---|---|---|
| 3,579,533 | 5/1971 | Yalman | 260/314 |
| 4,284,562 | 8/1981 | Anderson et al. | 260/326.2 |
| 5,002,962 | 3/1991 | Pandey et al. | 514/410 |
| 5,241,062 | 8/1993 | Wijesekera et al. | 540/145 |

FOREIGN PATENT DOCUMENTS

| | | |
|---|---|---|
| 0 025 884 A1 | 4/1981 | European Pat. Off. . |
| 0 471 561 A2 | 2/1992 | European Pat. Off. . |

OTHER PUBLICATIONS

E.H. Rodd (Ed)., Chemistry of Carbon Compounds vol. IV., p. 1119., Elsevier Publishing, Co., 1959 Campestrini et al., Inorg. Chem., 31, pp. 1999–2006., 1992.
Copy of the European Search Report dated May 4, 1999, 3 pages.

*Primary Examiner*—Richard L. Raymond
*Assistant Examiner*—Pavanaram K Sripada
*Attorney, Agent, or Firm*—Woodcock Washburn Kurtz Mackiewicz & Norris LLP

[57] ABSTRACT

Electron-deficient porphyrins are provided, as well as processes and intermediates for their preparation. In preferred embodiments, the electron-deficient porphyrins are prepared by condensing pyrrole derivatives and removing water thus formed from the resulting reaction mixture.

8 Claims, No Drawings

ELECTRON-DEFICIENT PORPHYRINS AND PROCESSES AND INTERMEDIATES FOR PREPARING SAME

RELATED APPLICATIONS

This application is a divisional U.S. Ser. No. 08/763,766, filed Dec. 11, 1996, now issued as U.S. Pat. No. 5,856,515 which is a divisional of U.S. Ser. No. 08/234,651, filed Apr. 28, 1994, now issued as U.S. Pat. No. 5,599,924 which is a continuation-in-part of U.S. Ser. No. 08/064,468, filed May 20, 1993 now issued as U.S. Pat. No. 5,493,017, which is a continuation-in-part of U.S. Ser. No. 07/929,943, filed Aug. 14, 1992 now issued as U.S. Pat. No. 5,371,199.

FIELD OF THE INVENTION

This invention relates to porphyrins bearing electron-withdrawing substituents such as perhaloalkyl groups, and to techniques and intermediates useful in preparing such compounds.

BACKGROUND OF THE INVENTION

Porphyrins are derivatives of porphine, a conjugated cyclic structure of four pyrrole rings linked through their 2- and 5-positions by methine bridges. Porphyrins can be covalently attached to other molecules. The electronic features of the porphyrin ring system can be altered by the attachment of one or more substituents. The term "porphyrin" includes derivatives wherein a metal atom is inserted into the ring system, as well as molecular systems in which ligands are attached to the metal. The substituents, as well as the overall porphyrin structure, can be neutral, positively charged, or negatively charged.

Electron-deficient porphyrins (i.e., porphyrins bearing substituents that are electron-withdrawing relative to hydrogen) have been suggested for use as industrial oxidation catalysts. A number such compounds have been prepared, typically through condensation of suitably substituted aldehydes and/or pyrroles. However, known synthetic methods generally proceed in low yield, if at all, and cannot be used to produce many types of electron-deficient porphyrins. Accordingly, there exists a need in the art for efficient synthetic methods capable of producing a greater variety of such compounds.

OBJECTS OF THE INVENTION

It is one object of the present invention to provide improved methods for synthesizing electron-deficient porphyrins.

It is another object of the invention to provide novel electron-deficient porphyrins.

It is yet another object to provide novel compounds that include electron-deficient porphyrins.

It is yet another object to provide synthetic precursors of electron-deficient porphyrins.

It is a further object of the invention to provide polymers containing linked electron-deficient porphyrins.

It is still another object to provide new applications for electron-deficient porphyrins and compounds that contain them.

SUMMARY OF THE INVENTION

These and other objects are satisfied by the present invention, which provides novel electron-deficient porphyrins and methods for their preparation. In preferred embodiments, the electron-deficient porphyrins have formula (1), (2), or (3):

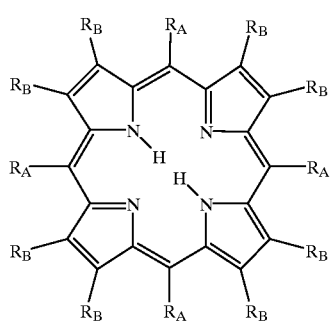

(1)

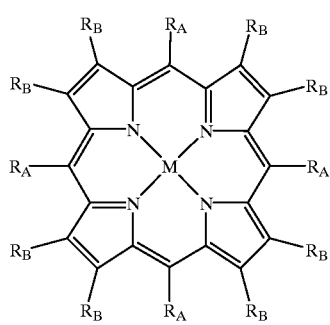

(2)

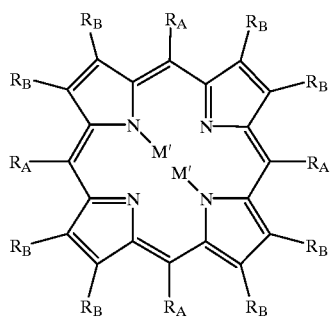

(3)

wherein M and M' are metal atoms and at least one of $R_A$ is a group that is electron-withdrawing relative to hydrogen. In preferred embodiments, at least one $R_A$ is a perhaloalkyl group or a perhaloaryl groups and at least one $R_B$ group is H, perhaloalkyl, perhaloaryl, $NO_2$, F, Cl, Br, or CN.

In accordance with the invention, these and other electron-deficient porphyrins are prepared by first preparing an electron-deficient porphyrinogen, a partially-oxidized, electron-deficient porphyrinogen, an electron-deficient polypyrryl intermediate, or a partially-oxidized, electron-deficient polypyrryl intermediate (together, porphyrinogens and polypyrryl intermediates) through pyrrole-based condensation reactions wherein at least a portion of the generated water in such reactions is removed from the reaction mixture. In certain embodiments, porphyrincogens and polypyrryl intermediates are prepared by condensing an aldehyde having formula $R_A$—CHO with a pyrrole derivative having formula (4) (q=0, 1, or 2). Alternatively, such compounds are prepared by condensing hydroxymethylpyrrole having formula (5) (n=0, 1, or 2).

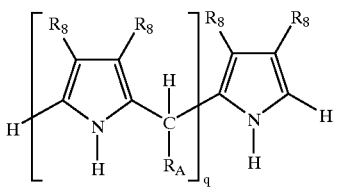

(4)

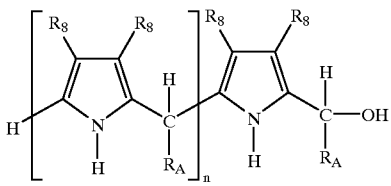

(5)

Porphyrinogens and polypyrryl intermediates also can be prepared by condensing bis-hydroxymethylpyrrole having formula (6) (n=0, 1, or 2) with a pyrrole having formula (7).

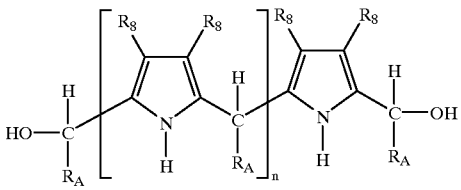

(6)

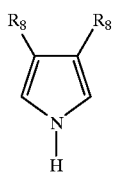

(7)

Porphyrinogens and polypyrryl intermediates thus formed can be directly oxidized or can be isolated and then oxidized. Oxidation of porphyrinogens yields porphyrins and/or partially oxidized porphyrinogens. Oxidation of polypyrryl intermediates yields partially-oxidized polypyrryl intermediates that can be further condensed and/or oxidized to form porphyrins, porphyrinogens, and/or further polypyrryl intermediates.

In another aspect, the invention provides polymers comprising linked porphyrin units, at least one of such units being an electron-deficient porphyrin. In certain embodiments, porphyrin units having formula (1), (2), or (3) share covalent bonds. In other embodiments, at least one $R_A$ group or $R_B$ group functions as a linking group In these embodiments, at least a portion of a linking group can have formula $[C(R_C)=C(R_D)(R_E)]_x$, $[C\equiv C(R_D)]_x$, $[CH_2(R_C)-CH(R_D)(R_E)]_x$ or $[CH=CH(RD)]_x$ where $R_C$, $R_D$, and $R_E$ are, independently, H, F, Cl, Br, I, alkyl or heteroalkyl having from 1 to about 20 carbon atoms, aryl or heteroaryl having about 4 to about 20 carbon atoms, alkenyl or heteroalkenyl having from 1 to about 20 carbon atoms, alkynyl or heteroalkynyl having from 1 to about 20 carbon atoms, trialkylsilyl or porphyrinato, provided that at least one of $R_C$, $R_D$, and $R_E$ is not H and x is at least 1. $R_C$, $R_D$, and $R_E$ also can include peptides, nucleosides, and/or saccharides. The remaining of $R_A$ and $R_B$ can be H, halogen, alkyl or heteroalkyl having 1 to about 20 carbon atoms or aryl or heteroaryl having 4 to about 20 carbon atoms, $C(RC)=C(R_D)(R_E)$, $C\equiv C(R_D)$, or a chemical functional group that includes a peptide, nucleoside, and/or saccharide. In other preferred embodiments, the linking group is cycloalkyl or aryl having about 6 to about 22 carbon atoms.

The invention also provides processes for preparing porphyrin-containing polymers. In certain embodiments, the processes comprise providing at least two compounds that, independently, have formula (1), (2), or (3) wherein at least one $R_A$ group or $R_B$ group in each of the compounds contains an olefinic carbon-carbon double bond or a chemical functional group reactive therewith. In other embodiments, at least one $R_A$ group or $R_B$ group in each of the compounds contains a carbon-carbon triple bond or a chemical functional group reactive therewith. The compounds are then contacted for a time and under reaction conditions effective to form covalent bonds through the carbon-carbon double and/or triple bonds.

The porphyrins and porphyrin-containing polymers of the invention can be used, for example, as dyes, catalysts, contrast agents, antitumor agents, antiviral agents, and in chemical sensors and electrooptical devices.

DETAILED DESCRIPTION OF THE INVENTION

It has been found in accordance with the present invention that a wide variety of novel porphyrins can be prepared by condensation of suitably functionalized pyrroles provided that at least a portion of the water of condensation is removed from the reaction mixture. In general, the resulting porphyrins have formula (1), (2), or (3):

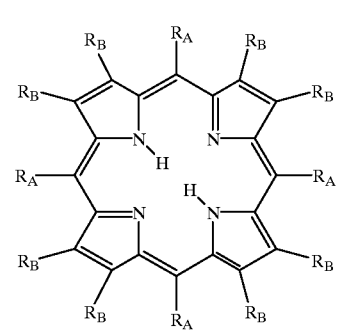

(1)

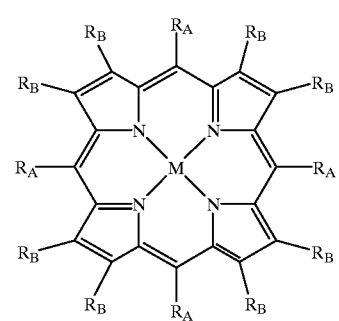

(2)

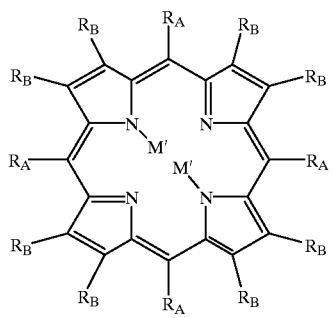

(3)

wherein M and M' are metal atoms, at least one $R_A$ is a group that is electron-withdrawing relative to hydrogen, and at least one $R_B$ is H or an acid-stable chemical functional group.

M preferably is a lanthanide or actinide or a metal such as Sc, Ti, V, Cr, Mn, Fe, Co, Ni, Cu, Y, Zr, Nb, Mo, Ru, Rh, Pd, Ag, La, Hf, Ta, W, Re, Os, Ir, Pt, Cd, Hg, Li or Au. More preferably, M is Cr, Mn, Fe, Co, Ni, Ru, Rh, Pd, Os, Ir, Pt, or Au. M' can be a metal such as Li, Na, K, Rb, or Cs, preferably Li.

At least one $R_A$ in the compounds of the invention is an alkyl group that is electron-withdrawing relative to hydrogen. The remaining $R_A$ and $R_B$ groups can be the same or is different and are selected from H and those groups known to be stable under the acidic reaction conditions of the invention, including alkyl, alkenyl, alkynyl, and aryl groups. (see, e.g., Application Ser. No. 08/064,468). In preferred embodiments, the $R_A$ groups are selected such that they are not each perhaloalkyl having 1 to 4 carbon atoms, phenyl, dihalophenyl, perhalophenyl, or CN, and the $R_B$ groups are selected such that they are not perfluoromethyl, $NO_2$, CN, or halogen. Those skilled in the art will recognize that chemical protecting groups can be attached to acid-sensitive functionality found within $R_A$ and/or $R_B$ and can be removed after condensation has been completed. (see, e.g., Greene and Wuts in *Protective Groups in Organic Synthesis,* John Wiley & Sons, Inc., 1991).

Compounds having formulas (1)–(3) preferably bear 1, 2, 4, 8, or 12 substituents (i.e., 1, 2, 4, 8, or 12 of $R_A$ and $R_B$ are not H). In certain embodiments, four $R_A$ groups bear electron-withdrawing functionality.

Numerous examples of electron-withdrawing functional groups are known to those skilled in the art. Further, electron-withdrawing groups can be identified through routine experimentation involving, for example, replacement of hydrogen in a molecule with a given group and then testing any resultant inductive effects. Representative electron withdrawing groups include the following: N—(alkyl)$_3^+$, $NH_3^+$, $NO_2$, $SO_2$—(alkyl), CN, $SO_2$—(aryl), C(O)OH, F, Cl, Br, I, C(O)O—(alkyl), C(O)—(alkyl), and/or CHO, where n alkyl groups have from about 1–30 carbon atoms and aryl groups have about 3–50 carbon atoms. In preferred embodiments, alkyl and aryl groups have from 1 to about 20 carbon atoms and about 6 to about 20 carbon atoms, respectively. More preferably, alkyl groups have from 5 to about 20 carbon atoms and aryl groups have from about 6 to about 20 carbon atoms. The terms alkyl and aryl are intended to include moieties substituted with, for example, halogens or nitro groups, as well as moieties wherein heteroatoms (e.g., N, O, S, Se, and Te) are inserted into the carbon backbone of an alkyl or aryl structure to yield, for example, an ether, thioether, and pyridinyl group. Alkyl and aryl groups can bear substituents that include additional carbon atoms. Preferred electron-withdrawing groups are substituted and unsubstituted alkyl and aryl groups that possess net electron-withdrawing effects. Perhaloalkyl and perhaloaryl groups are particularly preferred, including perfluoroalkyl, perfluorophenyl, perfluorobenzyl, and tetrafluoropyridyl groups.

In certain embodiments, porphyrins according to the invention are prepared by synthesizing and then oxidizing suitably-substituted porphyrinogen compounds having, for example, formulas (8) and (9).

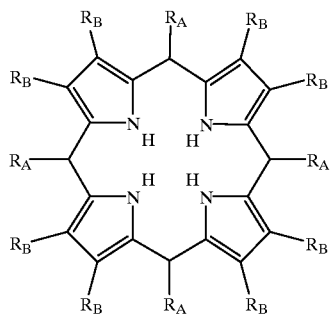

(8)

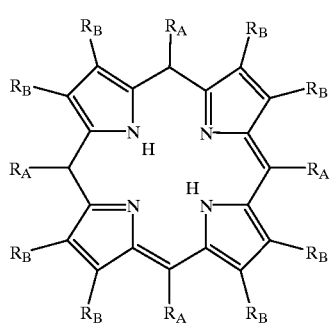

(9)

In other embodiments porphyrins are prepared by condensation and oxidation of suitably-substituted polypyrryl intermediates having, for example, formulas (10) and (11).

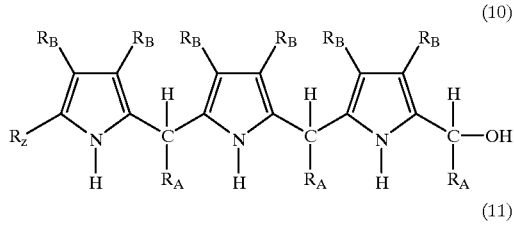

(10)

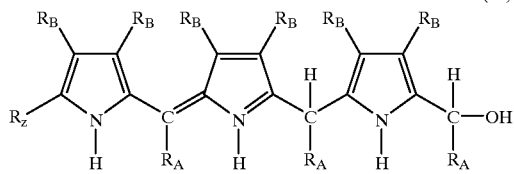

(11)

Porphyrinogens and polypyrryl intermediates can be prepared by condensing aldehydes having formula $R_A$—CHO with pyrroles derivative having formula (4) (q=0, 1, or 2). Alternatively, such compounds are prepared by condensing alcohols having formula (5) (n=0, 1, or 2)

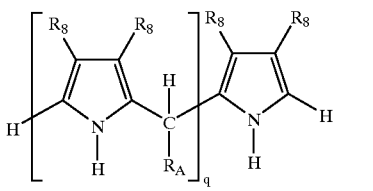
(4)

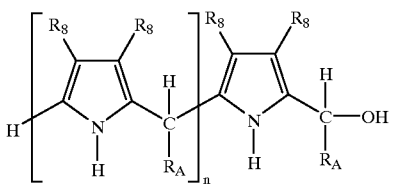
(5)

Porphyrinogens and polypyrryl intermediates also can be prepared by condensing alcohols having formula (6) (n=0, 1, or 2) with pyrroles having formula (7).

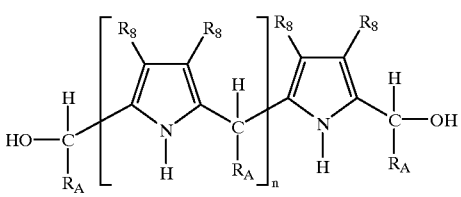
(6)

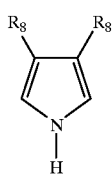
(7)

Each of these reactions should be performed in organic solvent in the presence of acid for a time and under conditions effective to form a reaction mixture comprising water and an adduct of the reagents. In accordance with the invention, at least a portion of the water thus formed is removed from the reaction mixture.

A wide variety of organic solvents can be used in the synthetic processes of the invention, including benzene, toluene, xylenes, methylene chloride, chloroform, trichlcroethylene, and mixtures thereof. Aprotic solvents are preferred, particularly nonpolar, aprotic solvents. Solvents capable of forming azeotropes (i.e., constant boiling mixtures) with water are particularly preferred.

Acids according to the invention are ions or molecules having the capacity to accept at least one electron pair. Representative acids include benzoic acid, sulfonic acids (e.g., p-toluenesulfonic acid and methanesulfonic acid), trifluoracetic acid, boron trifluoride, boron trichloride, and mixtures thereof. Preferred acids are not volatile under reactions conditions of the invention. Protic acids, particularly strong protic acids (i.e., those having $pK_a<0$), are preferred. In preferred embodiments, a catalytic (i.e., non-stoichiometric) amount of acid is used.

Water can be removed from adduct-containing reaction mixtures by a wide variety of known techniques, including membrane-based separations. Water also can be removed by contacting a reaction mixture with moieties that absorb, trap, or react with water or otherwise render water non-reactive. In general, the chosen technique should remove at least a portion of any water present but should not remove the adduct-forming reagents. Representative water removal techniques are disclosed by U.S. Pat. No. 4,332,643 (Reid, European Patent Application EP 92-114390 (Inaba, et al.), Japanese Patent Applications 91-146674 (Miyazaki, et al.), 91-20083 (Kondo, et al.), and 90-104128 (Okazaki, et al.), and Brazilian Patent Application 77-433 (Scaglia, et al.). Water preferably is removed by distilling an azeotrope formed by the water and the organic solvent. In certain embodiments, the distilled azeotrope is collected in a vessel and allowed to separate into aqueous and organic phases, and the organic (solvent) phase is returned to the reaction mixture. In other embodiments, the distilled azeotrope is contacted with a drying agent and the dried distillate is returned to the reaction mixture. Representative drying agents include phosphorous pentoxide, calcium hydride, calcium oxide, barium oxide, lithium aluminum hydride, molecular sieves, and mixtures thereof. Numerous additional drying agents are well-known to persons of ordinary skill in the art. In further embodiments, the dried distillate is collected and a roughly equal volume of fresh solvent is added to the reaction mixture. In still further embodiments, semi-permeable membrane technology is used to remove water from the reaction mixture as it is formed.

Hydroxymethylpyrroles having formulas (5) and (6) preferably prepared by contacting a pyrrole having formula (7) with base in organic solvent in the presence of an aldehyde having formula $R_A$—CHO. Representative bases include sodium hydroxide, lithium hydroxide, potassium hydroxide, barium hydroxide, alkyl or aryl lithium reagents, and alkyl or aryl Grignard reagents, with sodium hydroxide being preferred. The pyrrole, aldehyde, and base can be reacted simultaneously or in a number of different ways. For example, the pyrrole can be contacted with base and then added to the aldehyde, or can be contacted with base in the presence of aldehyde. In certain embodiments, pyrrole, aldehyde, and base are contacted in the absence of solvent.

Oxidation of porphyrinogens and polypyrryl intermediates can be accomplished by a number of techniques. For example, porphyrinogen- and/or polypyrryl-containing reaction mixtures can be exposed to oxidizing conditions. Alternatively, such compounds are isolated from a reaction mixture and then contacted with an oxidizing agent. Representative oxidizing agents include oxygen, p-chloranil, 2,3-dichloro-5,6-dicyanobenzoguinone (DDQ), and mixtures. Oxidation of electron-deficient compounds also can be effected using bulk electrochemical methods (see, e.g., Laboroatory Techniques in Electroanalytical Chemistry, P. T. Kissinger and W. R. Heineman, eds., New York, Marcel Dekker, 1984). In general, oxidation conditions for partially-oxidized porphyrinogens and polypyrryl intermediates (e.g., formulas (9) and (11)) will be less vigorous than for porphyrinogens and polypyrryl intermediates in more reduced form (e.g., formulas (8) and (10)). More electron-deficient porphyrinogens generally require more vigorous oxidation conditions.

The processes of the invention produce somewhat monomeric compounds that can be incorporates into porphyrin-containing homopolymers or copolymers or into macromolecular or supramolecular species containing, for example, one or more peptides, nucleosides, or saccharides. Polymers according to the invention can contain as few as 2 porphyrin units, but more preferably contain at least 3 porphyrin units, more preferably at least 5 porphyrin units. In certain embodiments, polymers of the invention comprise a plurality of porphyrin units that, independently, have formula (1), (2), or (3) wherein at least one $R_A$ group or $R_B$ group includes a linking group selected from $[C(R_C)=C(R_D)(R_E)]_x$, $[C\equiv C(R_D)]_x$, $[CH_2(R_C)-CH(R_D)(R_E)]_x$ or $[CH=CH(R_D)]_x$ where x is at least 1. The remaining $R_A$ and $R_B$ include at least one group that is electron-withdrawing relative to hydrogen.

In other embodiments, polymers according to the invention comprise a plurality of porphyrin units that, independently, have formula (1), (2), or (3) wherein at least one $R_A$ group or $R_B$ group is a cycloalkyl, cycloalkenyl, aryl or heteroaryl linking group having about 6 to about 22 carbon atoms.

Those skilled in the art will recognize the wide variety of polymers that can be prepared from the porphyrin-containing compounds of the invention. In certain embodiments, cofacial polymers are forced having, for example, formula (12). (see, e.g., Durand, et al., *J. Am. Chem. Soc.*, 1983, 105, 2710).

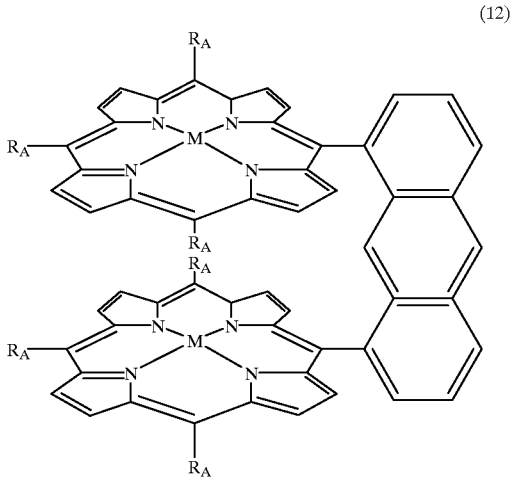

(12)

In other embodiments, somewhat linear polymer chains are formed wherein a portion of the polymer has general formula $(P_N)_r$ where $P_N$ is a porphyrin unit and r is at least 2. In further embodiments, linear polymer chains have general formula:

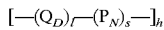

where $Q_L$ is a linking group, $P_N$ is a porphyrin unit, and h, l, and s are independently selected to be at least 1. For example, a portion of such polymers can have formula:

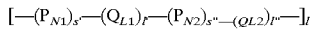

wherein $P_{N1}$ and $P_{N2}$ are independently selected porphyrin units, $Q_{L1}$ and $Q_{L2}$ are independently selected linking groups, and l', l", s', and s" are at least 1. These essentially linear polymer chains can be cross-linked such that a portion of the polymer has general formula:

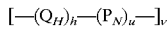

wherein $Q_H$ is a linking group, and h, u, and v are independently selected to be at least 1. A portion of these cross-linked polymers can have formula:

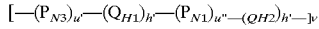

wherein $P_{N3}$ is a porphyrin unit, $Q_{H1}$ and $Q_{H2}$ are independently selected linking groups, and h', h", u', and u" are at least 1. Thus, cross-linked polymers can have formulas:

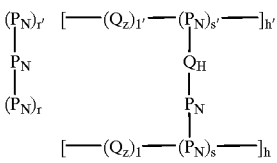

where r' is at least 1.

The polymers of the invention can be formed by contacting a substituted porphyrin with a second compound containing functionality that is reactive with the functionality contained within the porphyrin. Preferably, the porphyrin contains an olefinic carbon-carbon double bond, a carbon-carbon triple bond or some other reactive functionality. The contacting should be performed under conditions effective to form a covalent bond between the respective reactive functionalities. Preferably, porphyrin-containing polymers are formed by metal-mediated cross-coupling of, for example, dibrominated porphyrin units. Also, porphyrin-containing polymers can be synthesized using known terminal alkyne coupling chemistry. (see, e.g., Patai, et al., The Chemistry of Functional Groups, Supplement C, Part 1, pp. 529–534, Wiley, 1983; Cadiot, et al., Acetylenes, pp. 597–647, Marcel Dekker, 1964; and Eglinton, et al., *Adv. Org. Chem.*, 1963, 4, 225). As will be recognized, the second compound noted above can be a substituted porphyrin of the invention or some other moiety such as an acrylate monomer. Thus, a wide variety of copolymeric structures can be synthesized with the porphyrins of the invention. Through careful substituent selection the porphyrins of the invention can be incorporated into virtually any polymeric matrix known in the art; including but not limited to polyacetylenes, polyacrylates, polyolefins, polyethers, polyurethanes, polycarbonates, polyanilines, polypyrroles, and polythiophenes. For example, fluorescent porphyrins can be incorporated into such polymers as end-capping groups.

The porphyrins and porphyrin-containing polymers of the invention can be used, for example, as dyes, catalysts, contrast agents, antitumor agents, antiviral agents, liquid crystals, in chemical sensors and in electrooptical and solar energy conversion devices. One preferred use for compounds containing electron-deficient porphyrins are as catalysts for the oxygenation of alkanes and/or alkenes, particularly oxygenations performed in supercritical carbon dioxide. Electron-deficient porphyrins also can be incorporated into supramolecular structures. The polymers and supramolecular structures, which anchor porphyrin units in a relatively stable geometry, should improve many of the known uses for porphyrins and even provide a number of new uses, such as in a solid phase system for sterilizing virus-containing solutions. Representative uses are disclosed by, for example, the following patents, which are incorporated herein by reference: U.S. Pat. No. 4,895,682 (Ellis, et al.); U.S. Pat. No. 4,986,256 (Cohen); U.S. Pat. No. 4,668,670 (Rideout, et al.); U.S. Pat. No. 3,897,255 (Erickson); U.S. Pat. No. 3,899,334 (Erickson); U.S. Pat. No. 3,687,863 (Wacher); U.S. Pat. No. 4,647,478 (Formanek, et al.); and U.S. Pat. No. 4,957,615 (Ushizawa, et al.). Further uses are disclosed are disclosed by, for example, U.K. Patent Application 2,225,963 (Casson, et al.); International Application WO 89/11277 (Dixon, et al.); International Application WO 91/09631 (Matthews, et al.); European Patent Application 85105490.8 (Weishaupt, et al.); European Patent Application 90202953.7 (Terrell, et al.); European Patent Application 89304234.1 (Matsushima, et al.); Lehn, *Angew. Chem. Int. Ed. Engl.,* 1988, 27, 89; Wasielewski, *Chem. Rev.,* 1992, 92, 435; Mansury, et al., *J. Chem. Soc., Chem. Comm.,* 1985, 155; Groves, et al., *J. Am. Chem. Soc.,* 1983, 105, 5791; and Giroud-Godquin, et al., *Angew. Chem. Int. Ed. Engl.,* 1991, 30, 375. It is believed that the porphyrins of the invention can be substituted for the porphyrins disclosed in each of the foregoing publications.

Additional objects, advantages, and novel features of this invention will become apparent to those skilled in the art upon examination of the following examples thereof, which are not intended to be limiting.

EXAMPLE 1

Preparation Of 2-(2,2,3,3,4,4,4-Heptafluoro-1-hydroxybutyl)pyrrole From Heptafluorobutyraldehyde Hydrate Heptafluorobutyraldehyde hydrate (9.26 g, 42.9 mmol) was placed in a 100 mL Schlenk flask. This was frozen with liquid nitrogen and an inert atmosphere was established. Against an outflow of nitrogen, dried pyrrole (5.95 mL, 85.8 mmol) and sodium hydroxide (4.52 g, 113 mmol) were added. The flask was wrapped in foil and the mixture was stirred overnight, during which time it solidified. A colorless liquid also was present. The volatiles were removed by vacuum, leaving a light brown solid. The solid was dissolved in 40 mL of water and the solution was extracted (4×50 mL) with methylene chloride. The organic layers were dried over sodium sulfate and then evaporated to dryness under vacuum to give 5.39 g (47%) of a light yellow-brown solid. $^1$H NMR, (CDCl$_3$, 360 MHz) d 8.50 br 1H; 6.87 m 1H; 6.32 m 1H; 6.22 m 1H; 5.28 d, J=8.17 Hz; 5.23 d, J=7.67 Hz; 2.42 br s.

EXAMPLE 2

Preparation Of 2-(2,2,3,3,4,4,4-Heptafluoro-1-hydroxybutyl)pyrrole From Using Organolithium Reagents Dry, distilled pyrrole (80 mmol) is dissolved in diethyl ether (200 ml) and cooled to −78° C. Butyl lithium (80 mmol, 32 ml of 2.5 M solution in hexane) is added dropwise with stirring and the solution is gradually warmed to room temperature with evolution of hydrogen. This solution is transferred dropwise by cannula to a −78° C. solution of dry heptafluorobutyraldehyde (previously distilled from P$_2$O$_5$) in tetrahydrofuran (THF). The solution is warmed to room temperature with stirring. The volatiles are removed by vacuum leaving a solid that is dissolved in 40 mL of water and extracted (4×50 ml) with methylene chloride. The organic layers are dried over sodium sulfate and then evaporated to dryness under vacuum to give the product.

EXAMPLE 3

Preparation Of 2,5-Bis(2,2,3,3,4,4,4-heptafluoro-1-hydroxybutyl)pyrrole

Heptafluorobutyraldehyde hydrate (5.0 g, 23 mmol) was placed in a 100 mL Schlenk flask. This was frozen with liquid nitrogen and an inert atmosphere was established. Against an outflow of nitrogen, dried pyrrole (0.694 mL, 10 mmol) and sodium hydroxide (2.25 g, 56 mmol) were added. The flask was wrapped in foil and the mixture was stirred for 2 days. The volatiles were removed by vacuum, leaving a light brown, oily solid. The solid was dissolved in 40 ml of water and the solution was extracted (4×50 ml) with methylene chloride. The organic layers were dried over sodium sulfate and then evaporated to dryness under vacuum to an oily brown solid (38%), which proved to be a diastereomeric mixture of the desired products.

EXAMPLE 4

Preparation Of 2-(2,2-Difluoro-2-pentafluorophenyl-1-hydroxyethyl)pyrrole

2-Pentafluorophenyl-2,2-difluoroethanal (40 mmol) and THF (5 ml) are placed in a 100 mL Schlenk flask. This is frozen with liquid nitrogen and an inert atmosphere is established. Against an outflow of nitrogen, dried pyrrole (5.95 mL, 85.8 mmol) and sodium hydroxide (4.52 g, 113 mmol) is added. The flask is wrapped in foil and the mixture is stirred overnight. The volatiles are removed by vacuum, the resulting solid is dissolved in 40 mL of water, and the solution is extracted (4×50 ml) with methylene chloride. The organic layers are dried over sodium sulfate and then evaporated to dryness under vacuum to give 2-(2,2-difluoro-2-pentafluorophenyl-1-hydroxyethyl)pyrrole.

EXAMPLE 5

Preparation Of 2-(2,2,2-Trifluoro-1-hydroxyethyl)pyrrole

The procedure of Example 4 is repeated except that trifluoroacetaldehyde is used in place of 2-Pentafluorophenyl-2,2-difluoroethanal.

EXAMPLE 6

Preparation Of 2-Pyrrolylperfluoroundecyl Methanol

The procedure of Example 4 is repeated except that perfluorododecanal is used in place of 2-Pentafluorophenyl-2,2-difluoroethanal.

EXAMPLE 7

Preparation Of Tetrakis(heptafluoropropyl)porphyrin From 2-Pyrrolyperfluoropropyl Methanol Benzene (650 ml) was placed in a one liter, double-necked flask and azeotropically dried under nitrogen using a recycling Dean-Stark apparatus. p-Toluenesulfonic acid hydrate (50 mg) was added to the benzene and azeotropic distillation was continued until the distillate stopped phase separating. The Dean-Stark trap was emptied and 4 Å molecular sieves (20 ml) were added to the trap. Distillation was continued for 10 minutes with the distillate recycling through the molecular sieves. 2-Pyrrolylperfluoropropylmethanol (265 mg, 1 mmol) was dissolved in 10 ml of dry benzene and added (all at once) to the benzene solution heated at reflux. The solution became pink immediately after the addition, then gradually darkened. Heating was continued for 30 minutes and the reaction mixture was quenched with 600 mg of DDQ. Heating was continued for an additional hour under N$_2$. The solution was transferred to a 1 liter round bottom flask and the solvent was removed and recovered by rotary evaporation. The remaining dark brown residue was dissolved, to the extent possible, in 50 ml of warm hexane containing 1 ml of pyridine, and was poured directly on to a short (2×10 cm) column consisting of silica that was packed in hexane and topped with a 2 cm pad of Celite. Elution of the porphyrin was carried out with hexane. Collection was continued until the eluant became nearly colorless. The solvent was removed from the collected fraction and the resulting solid was washed with cold hexane (10 ml) and filtered to yield 90 mg (37%) of nearly pure 5,10,15,20-tetrakis(perfluoropropyl)porphyrin. An analytical sample was recrystallized from chloroform (−20° C.) to yield crystals suitable for X-ray diffraction. $^1$H NMR (360 mHz, CDCl$_3$) d 9.50 (s, 8 H); −2.30 (s, 2 H). $^{19}$F NMR (DCDl$_3$ CF$_3$COOH ext. std) d −79.7 (t, 3 F); −80.9 (broad s, 2 F); −118.8 (broad s, 2 F). The $^{19}$F spectrum shows evidence of exchange behavior. The signal at −118.8 ppm sharpens to a broadened triplet upon warming the solution to 55° C. $^{13}$C NMR (75 MHz, CDCl$_3$) gave only two discernable signals at 144.2 and 133.8 after a 16 hour run.

EXAMPLE 8

Preparation Of Tetrakis(heptafluoropropyl)porphyrin From Pyrrole And Heptafluorobutyraldehyde In a procedure analogous to that described in Example 7, the apparatus was charged with benzene (650 ml), p-toluenesulfonic acid hydrate (50 mg) and heptafluorobutyraldehyde hydrate (0.22g, 1 mmol). After refluxing the mixture for 1 hour, dry pyrrole (70 μl, 1 mmol) was added. The reaction was monitored by thin layer chromatography (TLC); after 1.5 hours the reaction was quenched as in Example 7. The reaction mixture was neutralized with pyridine, filtered through silica gel, pumped dry, and further purified by chromatography on silica. Several pyrrole-containing products can be isolated from this preparation. The desired product, tetrakis(heptafluoro)porphyrin, eluted as the first colored band. This method gives 4 mg (1.6%) of the target porphyrin.

EXAMPLE 9

Preparation of Tetrachloroporphine

Porphine (Zn) (40 mg) was dissolved in 300 ml of a 1:1 mixture of THF and CHCl$_3$, and the mixture was placed in a 500 ml round bottomed flask. N-Chlorosuccinimide (NCS) was added (4.2 eq.) and the mixture was stirred overnight protected from the light. The reaction was monitored by TLC and four intermediates were observed, presumably the target compound and the mono-, di-, and trichloro intermediates. After 24 hours the reaction was stopped and tetrachloroporphine (>80%) was isolated.

EXAMPLE 10

Preparation Of Cofacial Porphyrin Dimers

To a THF solution of 5-bromo-10,15,20-trichloroporphyrinate (Zn) (1 eq.) is added Pd$^D$ bis (triphenylphosphine) (5 mol %) and anthracene-1,8-bis (chlorozinc) (0.5 eq). The reaction is stirred for 24 hours at room temperature. One band is evident by TLC of the reaction mixture. The compound is purified by silica cel chromatography to isolate the dimeric, anthracene bridged compound.

Those skilled in the art will appreciate that numerous changes and modifications may be made to the preferred embodiments of the invention and that such changes and modifications may be made without departing from the spirit of the invention. For example, it is believed that the methods of the present invention can be practiced using porphyrin-related compounds such as chlorins, phorbins, bacteriochlorins, porphyrinogens, sapphyrins, texaphrins, and pthalocyanines in place of porphyrins. It is therefore intended that the appended claims cover all such equivalent variations as fall within the true spirit and scope of the invention.

What is claimed is:
1. A compound having formula:

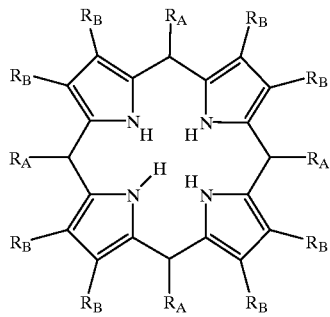

wherein:
at least one $R_A$ is an alkyl group that is electron-withdrawing relative to hydrogen; and
at least one $R_B$ is H or an acid-stable functional group.
2. A compound having formula (1), (2), or (3):

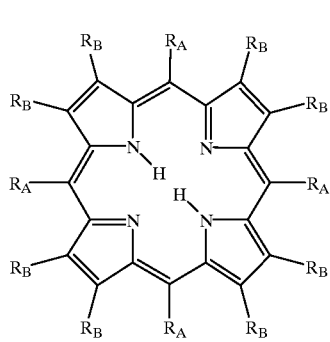

(1)

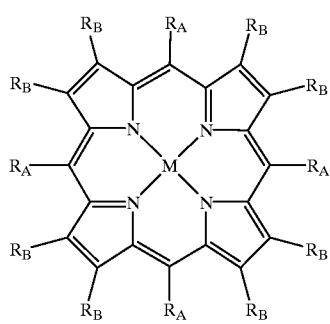

(2)

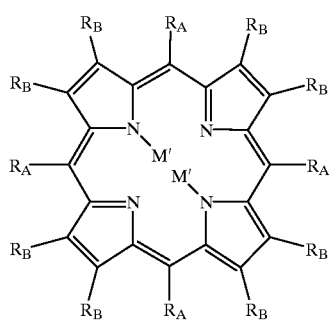

(3)

wherein:
at least one $R_A$ is an alkyl group that is electron-withdrawn relative to hydrogen;
at least one $R_B$ is H or an acid-stable functional group; and M and M' are metal atoms.

3. A polymer comprising a plurality of linked porphyrin units, wherein:

each of said porphyrin units, independently, has formula (1), (2), or (3);

M and M' are metal atoms;

at least one $R_A$ is an alkyl group that is electron-withdrawing relative to hydrogen; and at least one of RA and $R_B$ includes a linking group that is: aryl having 3 to about 50 carbon atoms, $[C(R_C)=C(R_D)(R_E)]_x$, $[C\equiv C(R_D)]_x$, $[CH_2(R_C)-CH(R_D)(R_E)]_x$ or $[CH=CH(R_D)]_x$ where n is at least 1, where $R_C$, $R_D$, and $R_E$ are, independently, H, F, Cl, Er, I, alkyl having from 1 to about 30 carbon atoms, aryl having about 3 to about 50 carbon atoms, alkenyl having from 1 to about 30 carbon atoms, alkynyl having from 1 to about 30 carbon atoms, trialkylsilyl, porphyrinato or a chemical functional group comprising a peptide, nucleoside or saccharide; or cycloalkyl or aryl having about 10 to about 22 carbon atoms.

4. A process in which an alkane or alkene is selectively oxidized by contact with air or oxygen in the presence of a compound according to claim 1.

5. The process of claim 4 wherein said alkane or said alkene is dissolved in supercritical carbon dioxide.

6. In a process in which an alkane is selectively oxidized by contact with an oxidant in the presence of a catalyst comprising a Group IV(a) to VII transition metal coordination complex, the improvement wherein said complex comprises a compound according to claim 1.

7. A supported catalyst comprising a compound according to claim 1 on a solid support material.

8. A composition comprising a polymeric matrix that contains at least one compound according to claim 1.

* * * * *